United States Patent [19]

Shoop et al.

[11] Patent Number: 5,139,948
[45] Date of Patent: Aug. 18, 1992

[54] STRAIN OF TRICHOSTRONGYLUS COLUBRIFORMIS WITH IVERMECTIN AND THIABENDAZOLE RESISTANCE

[75] Inventors: Wesley L. Shoop, Somerville, N.J.; John R. Egerton, Salida, Colo.

[73] Assignee: Merck & Co., Inc., Rahway, N.J.

[21] Appl. No.: 506,311

[22] Filed: Apr. 9, 1990

[51] Int. Cl.$^5$ ............................................. C12N 1/38
[52] U.S. Cl. ................................... 435/244; 435/243; 435/245
[58] Field of Search ........................ 435/243, 244, 245

[56] References Cited

PUBLICATIONS

Maclean et al. J. Helminthology "The pathogenesis of benzimidazole-resistant and benzimidazole-susceptible strains of *Trichostrongylus colubriformis* in the Mongolian gerbil (*Meriones unguiculatus*)" 61: 179-189 (1987).
Shoop et al. J. Parasitology "Laboratory Selection of a Benzimidazole-Resistant Isolate of *Trichostrongylus colubriformis* For Ivermectin Resistance" 70(2) 186-189 (1990).
Giordano et al, Veterinary Parasitology 30 139-148 (1988).
Egerton J. Parasit. 74(4) 1988 614-617.
Prichard Veterinary Parasitology 4 1978 pp. 243-255.

*Primary Examiner*—Douglas W. Robinson
*Assistant Examiner*—Jane A. Williams
*Attorney, Agent, or Firm*—David L. Rose; Joseph F. DiPrima

[57] ABSTRACT

A novel strain of *Trichostrongylus colubriformis* has the unique characteristics of being significantly resistant to the effect of antihelmintic drugs, in particular the antihelmintic drugs ivermectin and thiabendazole. The novel strain of *T. colubriformis* was prepared by the serial passage of the helminth through sheep. Twenty passages of the helminth through sheep were adequate to impart resistance to oral therapy of 20 times that normally expected with ivermectin. The highly resistant parasite is useful to screen for antihelmintic agents with different modes of action than that of ivermectin or thiabendazole which represent two of the three major classes of modern, broad spectrum anthelmintics.

2 Claims, No Drawings

STRAIN OF *TRICHOSTRONGYLUS COLUBRIFORMIS* WITH IVERMECTIN AND THIABENDAZOLE RESISTANCE

BACKGROUND OF THE INVENTION

Resistance to anthelmintic drug therapy is occassionally observed in the wild but rarely developed in the laboratory. Egerton et al., *J. Parasit.* 24 614–617 (1988) discloses a laboratory derived strain of *Haemonchus contortus* resistant to ivermectin. Giordano et al, *Veterinary Parasitology* 30 139-148 (1988), discloses a strain of *T. colubriformis* which is only partially resistant to ivermectin. No disclosures are known of any laboratory derived strains of helminths resistant to both ivermectin and thiabendazole. These characteristics of the new strain of *T. colubriformis* make it particularly useful as an agent for the selection of antihelmintic compounds with novel modes of action.

SUMMARY OF THE INVENTION

The instant invention is concerned with a novel strain of *Trichostrongylus colubriformis* which has the unique characteristics of being highly resistant to both ivermectin and thiabendazole, two widely used anthelmintic agents. The novel strain of *T. colubriformis* is prepared by serial passage through a series of sheep treated with ivermectin. Thus, it is an object of this invention to describe the novel strain of *T. colubriformis*. A further object is to describe the process used to prepare and select for the novel strain. A still further object is to describe methods for using the novel strain to identify anthelmintic agents with modes of action different from ivermectin and thiabendazole. Still further objects will become apparent from reading the following description.

DESCRIPTION OF THE INVENTION

A novel strain of *Trichostrongylus colubriformis* which is at least 20 times more resistant to ivermectin and thiabendazole oral therapy has been developed.

To ensure the availability of the novel strain of *T. colubriformis*, samples of the novel helminth have been deposited in a cryopreserved state with the American Type Culture Collection at 12301 Parklawn Drive, Rockville, MD 20852 and have been assigned the accession number ATCC 40779.

The novel strain of *T. colubriformis* is prepared from a strain of the helminth known as the Badgery Creek isolate which was found in Australia in 1973 as a natural strain which had developed resistance to thiabendazole. Ivermectin resistance was cultivated in this strain by infecting sheep with the helminth and administering ivermectin to such sheep in sufficient amount to kill most, but not all of the helminth. The sheep were infected in pairs, one wether and one ewe, with from 19,000 to 21,000 infective stage larvae, preferably about 20,000 such larvae, and approximately 3 to 6 weeks later, preferably about 24 days, from 0.06 to 0.25 mg/kg, preferably about 0.06 mg/kg of ivermectin was orally administered, although parenteral administration is also possible. The helminth is allowed to develop in the presence of a dose of ivermectin which is lethal to 95% of the parasites. The parasite progresses through its cycle and produces eggs which are excreted in the feces of the sheep. The eggs are separated from the feces and allowed to develop into the infective larval stage by incubation at from 25° to 28° C. and high relative humidity, in excess of 90%, preferably at about 90–95% relative humidity. The next generation of the helminth was passed through another pair of ivermectin treated sheep to further develop the resistance characteristics. As necessary, the dosage of ivermectin is adjusted to maintain at least 95% reduction in parasite control, as monitored by fecal egg output.

After passage through twenty pair of sheep, the *T. colubriformis* strain isolated from the sheep feces was at least 20 times more resistant to ivermectin than the original strain. In addition, the helminth was tested and found to have retained its original thiabendazole resistance.

These unique characteristics of the new strain of *T. colubriformis* allow it to be used to screen potential anthelmintice agents which have a novel mechanism of action. Agents with the mechanism of action of the macrocyclic lactones such as ivermectin and other avermectin compounds or the milbemycins or the mechanism of action of the benzimidazole anthelmintics such as thiabendazole, will also be ineffective against the new strain of *T. colubriformis*. Anthelmintic agents that are effective against the new strain of helminths will likely possess a mechanism of action different from the avermectins and milbemycins and the benzimidazoles. This can be a very effective screening method for novel anthelmintice agents with significant commercial potential.

A fungal metabolite of *Penicillium paraherquei* was discovered to have full activity against the novel resistant strain of *T. colubriformis*, thus suggesting that it was an anthelmintic agent with a novel mechanism of action, different from the mechanisms of ivermectin and thiabendazole. The compound, paraherquamide, was further tested and found to be a potent broad spectrum anthelmintic and antiparasitic agent. The spectrum of activity, while broad, was different from the spectrum of activity for both ivermectin, thus confirming that the compound, paraherquamide, operated with a different mechanism of action than the other anthelmintic agents.

EXAMPLE

Selection Protocol

Sheep were raised helminth-free by bringing them indoors on the day of lambing, maintaining them in elevated pens, and observing strict sanitary procedures. For the $P_1$ parasite generation, 1 wether and 1 ewe each were inoculated orally with 20,000 infective-stage larvae ($L_3$) of the Badgery's Creek isolate (TcR) of *T. colubriformis*. TcR originated in Australia in 1973 as a field isolate having thiabendazole resistance (Waller et al., 1985). Ivermectin treatment was administered to each sheep on day 24 postinfection as a single oral dosage of 0.06 mg/kg in vehicle (40% [v/v] glycerol formal and 60% [v/v] propylene glycol). The dosage given to the first pair of sheep was chosen to reduce the fecal egg output by ≈95%.

To obtain the necessary number of $F_1$ $L_3$ for the next sheep pair, the total fecal egg outputs of the ewe and wether were collected separately on day 7 posttreatment and incubated at 27° C. and 90–95% relative humidity for 5-7 days for larval development. A total of 20,000 $F_1$ $L_3$ from the ewe and 20,000 $F_1$ $L_3$ from the wether were pooled and served as the source of infection for the next lamb pair. This entire sequence of events was carried out for 21 generations of worms in 42 sheep.

Each sequential dosage was determined individually by comparing egg output prior to treatment with egg output after treatment for each generation and adjusting the dosage given to the next pair of sheep so that ≈95% fecal egg reduction was maintained. The initial selection dosage of 0.06 mg/kg was sufficient through the $F_9$ generation, but subsequent parasite generations had to be exposed to increasing selection dosage levels of ivermectin as summarized: $P_1$–$F_9$, 0.06 mg/kg; $F_{10}$, 0.08 mg/kg; $F_{11}$–$F_{15}$, 0.1 mg/kg; $F_{16}$, 0.15 mg/kg; $F_{17}$–$F_{19}$, 0.2 mg/kg; and $F_{20}$, 0.25 mg/kg.

Twenty-five days after the scheduled ivermectin treatment, the $F_{16}$ generation was treated also with thiabendazole at 50.0 mg/kg (44 mg/kg would be expected to kill >95% of the worms in a susceptible strain) to confirm benzimidazole resistance.

Dose Titration

When the surviving adult $F_{20}$ generation had produced sufficient $F_{21}$ $L_3$, a dose titration comparing simultaneously the parent TcR and the selected $F_{21}$ isolate was done. Forty helminth-free lambs were allocated to 2 groups of 20 lambs each by restricted randomization based on sex and body weight. One group was inoculated with 20,000 TcR $L_3$/lamb and the second group was inoculated with 20,000 $F_{21}$ $L_3$/lamb. Twenty-one days postinfection the lambs in each group were assigned to 5 subgroups of 4 lambs each by restricted randomization on sex and body weight. Within the TcR isolate group each of the 5 subgroups was assigned at random to 1 of the following: ivermectin at 0.03, 0.04, 0.05, or 0.06 mg/kg or vehicle. Within the $F_{21}$ isolate group each of the 5 subgroups was assigned at random to 1 of the following: ivermectin at 0.06, 0.10, 0.15, or 0.25 mg/kg or vehicle. Treatments were administered as single oral solutions at 0.1 ml/kg in 40% glycerol formal and 60% propylene glycol. One week after treatment, all sheep were killed and the small intestine of each was removed and the residual nematode population counted. General methods for infection, treatment, and necropsy were as described by Egerton et al. (1979).

Statistical Methods

Frequency distributions of parasite counts in ruminants are positively skewed (nonnormal) and require normalization by transformation to apply parametric tests of significance. Thus, all residual worm burdens and dosage data were transformed to common logarithms before being analyzed by analysis of variance, Duncan's multiple range t-test, and linear regression.

RESULTS

Fecal egg output for $P_1$–$F_9$ was reduced by ≈95% after each ivermectin treatment. The first evidence of resistance was observed in the fecal output of the $F_{10}$ in which only 72.7% and 69.5% reduction in the wether and ewe, respectively, occurred. Drug selection had been increased to 0.08 mg/kg for the $F_{10}$, and at times subsequent further increases were made when fecal egg control fell below 95%. Thiabendazole treatment of the $F_{16}$ generation reduced fecal egg output only by 54.0% in the wether and 53.7% in the ewe, thereby confirming that resistance to the benzimidazoles remained at a high level. When oral ivermectin drug pressure was increased beyond the manufacturer's suggested use level of 0.2 mg/kg and then failed to control fecal egg production (the $F_{20}$ generation), the parent TcR was titrated side-by-side with its ivermectin-selected $F_{21}$ isolate.

The results of the comparative titration with ivermectin are summarized in Tables I and II. The parent TcR isolate was markedly less infective (P<0.01) than the $F_{21}$ as expected. The TcR isolate also responded near maximally at all dosages tested as would be expected for a sensitive isolate. The $F_{21}$ generation, however, demonstrated substantial resistance. At 0.06 mg/kg, 99% of the TcR isolate was eliminated, whereas only 2.4% of the selected $F_{21}$ generation was removed. Even at 0.25 mg/kg the selected $F_{21}$ did not reach a 95% removal and this dosage is higher than the use level suggested by the manufacturer. The slope (regression coefficient) of the calculated linear dose-response curve for TcR did not differ (P=0.4) from that of the linear dose-response curve for the selected $F_{21}$. The pooled regression coefficient ($b_p = -1.45881$) estimate was, therefore, used in subsequent calculations involving the parallel regression equations. As indicated by the calculated "expected" response (Table I), both response curves appear a reasonable fit, with that for the selected $F_{21}$ isolate somewhat more variable (as would be expected with an increased resistance factor). As the estimated response curves were deemed parallel (vide supra) the estimate of potency (and resistance factor) would be identical for all equivalent efficacy coordinates on the curves. Thus, the $F_{21}$ adult was ≈20-fold more resistant to ivermectin treatment than the adult TcR at any given dosage (Table II).

DISCUSSION

Herein, we have shown that a closed population of *T. colubriformis* exposed to ivermectin dosages designed to kill 95% of the population over the course of 20 generations required ≈20 times the amount of ivermectin needed to kill an equivalent number of the parent isolate. In so doing, this is the first laboratory-selected isolate of any species to have a combination of ivermectin and benzimidazole resistance.

Although comparative titration of the TcR and the $F_{21}$ isolate confirmed ivermectin resistance, it is clear that resistance actually developed prior to that latter generation. The 0.06 mg/kg dosage effectively eliminated ≈95% of the parasite population for the first 9 generations as evidenced by fecal egg output. The $F_{10}$ egg output, however, was reduced only ≈70%, and escalating dosages were used to keep egg output at the 95% control level. Thus, it would seem that the earliest detectable resistance appeared sometime around the 10th generation in this study.

TABLE I

Efficacy of ivermectin as a single oral dose against susceptible parent (TcR) and laboratory-selected resistant ($F_{21}$) isolates of *Trichostrongylus colubriformis*

| Dosage mg/kg | Number of sheep/group | % Efficacy TcR Observed | % Efficacy TcR Expected* | % Efficacy $F_{21}$ Observed | % Efficacy $F_{21}$ Expected* |
|---|---|---|---|---|---|
| 0 (control) | 4 | (2,937) + | — | (8,292) + | — |
| 0.03 | 4 | 97.6 ‡ | 97.4 | — | — |
| 0.04 | 4 | 98.3 ‡ | 98.3 | — | — |
| 0.05 | 4 | 98.5 ‡ | 98.8 | — | — |
| 0.06 | 4 | 99.3 ‡ | 99.0 | 2.4 ‡ | 22.2 |
| 0.10 | 4 | — | — | 53.8 ‡ | 63.1 |
| 0.15 | 4 | — | — | 83.6 ‡ | 79.5 |

TABLE I-continued

Efficacy of ivermectin as a single oral dose against susceptible parent (TcR) and laboratory-selected resistant ($F_{21}$) isolates of *Trichostrongylus colubriformis*

| Dosage mg/kg | Number of sheep/group | % Efficacy | | | |
|---|---|---|---|---|---|
| | | TcR | | $F_{21}$ | |
| | | Observed | Expected* | Observed | Expected* |
| 0.25 | 4 | — | — | 92.3 | 90.1 |

*Calculated from respective regression equations from Table II.

+ Geometric mean number of worms in control sheep.

‡ Reduction from control values, P < 0.05; Duncan's multiple range t-test.

TABLE II

Dose-response of ivermectin-susceptible parent (TcR) and laboratory-selected resistant ($F_{21}$) isolates of *Trichostrongylus colubriformis* to ivermectin

| | TcR* $\log \hat{Y} = -1.45881$ $\log X -0.33937$ | $F_{21}$ $\log \hat{Y} = -1.45881$ $\log X +2.02739$ |
|---|---|---|
| $ED_{90} \pm SE$ | 0.004 ± 0.006 | 0.081 ± 0.022 |
| $ED_{95} \pm SE$ | 0.019 ± 0.013 | 0.394 ± 0.113 |
| $ED_{99} \pm SE$ | 0.058 ± 0.030 | 1.187 ± 0.407 |

*Y, expected number of worms; X, dose, mg/kg.
Calculated from log SE as 1-term Taylor expansion mg/kg.

What is claimed is:

1. A strain of *Trichostrongylus colubriformis* ATCC 40779 which is resistant to the anthelmintic effects of ivermectin and thiabendazole.

2. The strain of claim 1 where the resistant strain of Trichosrongylus colubriformis has an $ED_{95}$ level of at least 0.394 mg/kg of ivermectin relative to the $ED_{95}$ of the non-resistant strain of 0.019 mg/kg.

* * * * *